(12) United States Patent
Yoneda et al.

(10) Patent No.: US 9,835,571 B2
(45) Date of Patent: Dec. 5, 2017

(54) X-RAY ANALYZER

(71) Applicant: SHIMADZU CORPORATION, Kyoto-shi, Kyoto (JP)

(72) Inventors: Tetsuya Yoneda, Kyoto (JP); Takao Marui, Kyoto (JP); Masashi Matsuo, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 52 days.

(21) Appl. No.: 14/876,302

(22) Filed: Oct. 6, 2015

(65) Prior Publication Data

US 2017/0097309 A1 Apr. 6, 2017

(51) Int. Cl.
*G01N 23/00* (2006.01)
*G01N 23/207* (2006.01)

(52) U.S. Cl.
CPC .................. *G01N 23/207* (2013.01)

(58) Field of Classification Search
CPC ..................................... G01N 23/207
See application file for complete search history.

(56) References Cited

U.S. PATENT DOCUMENTS

| 4,800,580 | A | * | 1/1989 | Houtman | G01N 23/207 250/370.01 |
| 5,724,401 | A | | 3/1998 | Kurtz et al. | |
| 2006/0023838 | A1 | * | 2/2006 | He | G01N 23/20016 378/81 |

FOREIGN PATENT DOCUMENTS

| JP | 01291148 A | 11/1989 |
| JP | 04324348 A | 11/1992 |
| JP | 2000-35409 A | 2/2000 |
| JP | 2005121528 A | 5/2005 |

OTHER PUBLICATIONS

Communication dated Aug. 23, 2016, from the Japanese Patent Office in counterpart application No. 2013-110011.

\* cited by examiner

*Primary Examiner* — Dani Fox
(74) *Attorney, Agent, or Firm* — Sughrue Mion, PLLC (57) ABSTRACT

The detection surface of each of a plurality of detection elements is arranged on an arc along a diffractometer circle (reference circle). This allows each detection element to detect X-rays diffracted by a specimen at the focal position. Because this prevents errors in the X-ray intensity detected by each detection element, more accurate diffraction information can be obtained. As a result, a more accurate analysis can be performed in less time by detecting X-rays diffracted by the specimen using a plurality of detection elements.

8 Claims, 6 Drawing Sheets

X-RAY ANALYZER

TECHNICAL FIELD

The present invention relates to an X-ray analyzer for analyzing specimens via exposure to X-rays.

BACKGROUND ART

An X-ray analyzer includes an X-ray source for exposing a specimen to X-rays, and a detector for detecting X-rays diffracted by the specimen. In this type of X-ray analyzer, an analysis is sometimes performed while moving the X-ray source and detector relative to each other along a reference circle centered on the specimen (the so-called diffractometer circle) (see, for example, Patent Document 1).

Figure 5A:
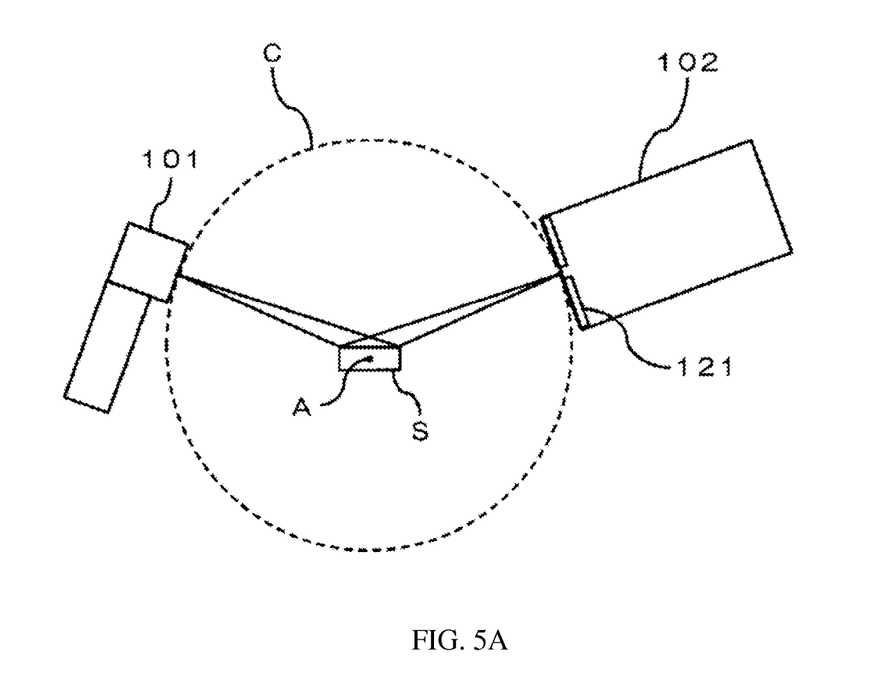
FIG. 5A is a schematic view showing the configuration of an X-ray analyzer of the prior art.

FIG. 5A is a schematic view showing the configuration of an X-ray analyzer of the prior art. In this example, the detector 102 includes a slit plate 121 with a slit of a predetermined width. Among the X-rays diffracted by the specimen S, the detector 102 only detects those X-rays which have passed through the slit in the slit plate 121. The X-ray source 101 and the slit plate 121 (slit) of the detector 102 are located on the diffractometer circle C centered on the specimen S.

During the analysis, the angle of incidence of the X-rays relative to the surface of the specimen S is changed by rotating the specimen S at a predetermined angular velocity (so-called θ rotation) using the center A of the diffractometer circle C as the axis of rotation. At this time, the detector 102 rotates at an angular velocity twice that of the θ rotation (so-called 2θ rotation) around the axis of rotation. In this way, diffraction information is obtained while holding constant the relationship between the angle of incidence of the X-rays relative to the specimen S and the angle of incidence to the slit of the X-rays diffracted by the specimen S.

When an analysis is performed using this type of X-ray analyzer, the slit plate 121 is moving continuously so that the slit moves along the diffractometer circle C. When the slit plate 121 has to be moved continuously so that X-rays passing through the slit at each slit position can be detected by the detector 102, the analysis takes a long time to complete. In recent years, X-ray analyzers have been developed which use a detector including a plurality of detection elements which move along the diffractometer circle C.

Figure 5B:
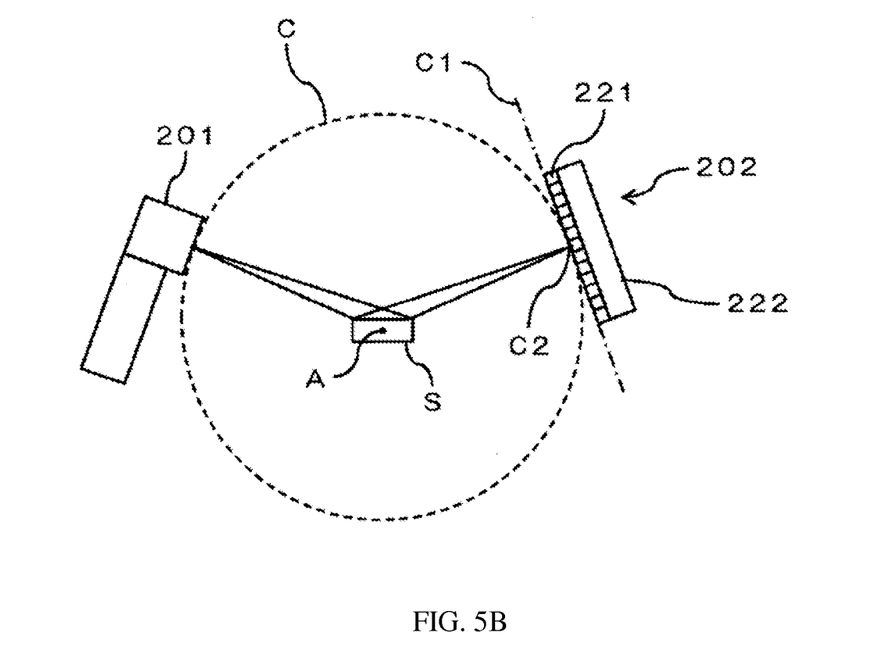
FIG. 5B is a schematic view showing another configuration of an X-ray analyzer of the prior art.

FIG. 5B is a schematic view showing another configuration of an X-ray analyzer of the prior art. In this example, a detector 202 is used in which a plurality of detection elements 221 are arranged in a single row on a substrate 222. The X-ray source 201 and the detector 202 are located on the diffractometer circle C centered on the specimen S. During analysis, the specimen S and the detector 202 are rotated in the manner mentioned above using the center A of the diffractometer C as the axis of rotation.

In the detector 202, each detection element 221 is aligned on tangent line C1 with the diffractometer circle C. In this X-ray analyzer, X-rays diffracted by the specimen S can be detected by the detection elements 221 at the same time. As a result, the analysis takes less time.

PRIOR ART DOCUMENTS

Patent Documents

[Patent Document 1] Laid-Open Patent Publication No. 2000-35409

SUMMARY OF THE INVENTION

Problem Solved by the Invention

However, a highly accurate analysis cannot be performed when a plurality of detection elements 221 are provided on a tangent line C1 of the diffractometer circle C. None of the detection elements 221 except for the detection element 221 at contact point C2 between the diffractometer circle C and the detector 202 are located on the diffractometer circle C, so the X-rays diffracted by the specimen S are detected at positions other than at the focal point. Therefore, errors occur in the X-ray intensity detected by each detection element 221, and accurate diffraction information sometimes cannot be obtained.

This problem occurs because the detection elements 221 are not at contact point C2, so the precision of the analysis decreases as the number of detection elements 221 on tangent line C1 increases. Therefore, because the number of detection elements 221 in the detector 202 cannot be increased, there are limits to how much the time required to perform an analysis can be reduced. In other words, it is difficult for an X-ray analyzer of the prior art to perform an accurate analysis in less time.

When diffraction information is obtained on the basis of X-ray intensities detected by each detection element 221, the position information of each detection element 221 is converted to angle information on the diffractometer circle C centered on the axis of rotation. Because all of the detection elements 221 not at contact point C2 are a certain distance from the diffractometer circle C, there are disparities in the angle information after conversion. Therefore, precise angle correction is required to perform an accurate analysis.

In light of this situation, it is an object of the present invention to provide an X-ray analyzer which is able to perform an accurate analysis in less time. It is another object of the present invention to provide an X-ray analyzer which is able to perform an accurate analysis without angle correction.

Means of Solving the Problem

The present invention is an X-ray analyzer including: an X-ray source for exposing a specimen to X-rays; a detector having a plurality of detection elements, each detection element detecting X-rays diffracted by the specimen; and a moving analysis mechanism for moving the X-ray source and detector relative to a reference circle centered on the specimen while performing an analysis, the detection surface of each detection element being located on an arc along the reference circle.

Because the detection surface of each detection element is located on an arc along the reference circle (diffractometer circle) in this configuration, each detection element detects X-rays diffracted by the specimen at the focal point. In this way, errors in the X-ray intensity detected by each detection element can be eliminated to obtain more accurate diffraction information. Because X-rays diffracted by the specimen are detected by a plurality of detection elements, an accurate analysis can be performed in less time.

Because the detection surface of each detection element is located on an arc along the reference circle, angle correction is not required to convert the position information of each detection element into angle information. As a result, an accurate analysis can be performed without angle correction.

The detection surface of each detection element may face the center of the reference circle.

In this configuration, the X-rays diffracted by the specimen are incident at a right angle on the detection surface of each detection element. In this way, errors in the X-ray intensity detected by each detection element are more effectively prevented, and an even more accurate analysis is performed.

The detector may be composed by arranging the plurality of detection elements in a single row on a flexible substrate. Here, the detection surface of each detection element is located on an arc along the reference circle by curving the flexible substrate.

In this configuration, the detection surface of each detection element can be positioned on an arc along the reference circle and the detection surfaces oriented towards the center of the reference circle simply by bending the flexible substrate. As a result, a very simple configuration for obtaining an accurate analysis can be realized.

The X-ray analyzer may also include an arc curvature changing mechanism for changing the curvature of the arc on which the detection surface of each detection element is located by moving the detection elements relative to each other.

In this configuration, because the curvature of the arc on which the detection surface of each detection element is located is changed, the incident aspect of the detection surface of each detection element can be changed relative to the X-rays diffracted by the specimen, and an analysis can be performed using a wider aspect.

The X-ray analyzer may also include a reference circle changing mechanism for changing the radius of the reference circle by moving the X-ray source and the detector relative to each other. Here, the arc curvature changing mechanism changes the curvature of the arc on which the detection surface of each detection element is located so as to correspond to the curvature of the reference circle changed by the reference circle changing mechanism.

In this configuration, the curvature of the arc on which the detection surface of each detection element is located can be changed to correspond to any change in the radius of the reference circle. For example, when the operator wishes to increase the resolution, the diameter of the reference circle can be increased, and the curvature of the arc on which the detection surface of each detection element is located can be increased accordingly. When the operator wishes to increase the X-ray intensity, the diameter of the reference circle can be decreased, and the curvature of the arc on which the detection surface of each detection element is located can be decreased accordingly. In both analytical modes, the curvature of the arc on which the detection surface of each detection element is located can be changed with great precision, and a more accurate analysis can be performed.

The present invention is also an X-ray analyzer including: an X-ray source for exposing a specimen to X-rays; a detector having a plurality of detection elements, each detection element detecting X-rays diffracted by the specimen; and a moving analysis mechanism for moving the X-ray source and detector relative to a reference sphere centered on the specimen while performing an analysis, the detection surface of each detection element being located on a spherical surface along the reference sphere.

Because the detection surface of each detection element is located on a spherical surface along the reference sphere (diffractometer sphere) in this configuration, each detection element detects X-rays diffracted by the specimen at the focal point. In this way, errors in the X-ray intensity detected by each detection element can be eliminated to obtain more accurate diffraction information. Because X-rays diffracted by the specimen are detected by a plurality of detection elements, an accurate analysis can be performed in less time.

Because the detection surface of each detection element is located on an arc along the reference sphere, angle correction is not required to convert the position information of each detection element into angle information. As a result, an accurate analysis can be performed without angle correction.

The detection surface of each detection element may face the center of the reference circle.

In this configuration, the X-rays diffracted by the specimen are incident at a right angle on the detection surface of each detection element. In this way, errors in the X-ray intensity detected by each detection element are more effectively prevented, and an even more accurate analysis is performed.

The detector may be composed by arranging the plurality of detection elements in a grid pattern on a flexible substrate. Here, the detection surface of each detection element is located on a spherical surface along the reference sphere by curving the flexible substrate.

In this configuration, the detection surface of each detection element can be positioned on a spherical surface along the reference sphere and the detection surfaces oriented towards the center of the reference sphere simply by bending the flexible substrate. As a result, a very simple configuration for obtaining an accurate analysis can be realized.

The X-ray analyzer may also include a spherical curvature changing mechanism for changing the curvature of the sphere on which the detection surface of each detection element is located by moving the detection elements relative to each other.

In this configuration, because the curvature of the spherical surface on which the detection surface of each detection element is located is changed, the incident aspect of the detection surface of each detection element can be changed relative to the X-rays diffracted by the specimen, and an analysis can be performed using a wider aspect.

The X-ray analyzer may also include a reference sphere changing mechanism for changing the radius of the reference sphere by moving the X-ray source and the detector relative to each other. Here, the spherical curvature changing mechanism changes the curvature of the sphere on which the detection surface of each detection element is located so as to correspond to the curvature of the reference sphere changed by the reference sphere changing mechanism.

In this configuration, the curvature of the spherical surface on which the detection surface of each detection element is located can be changed to correspond to any change in the radius of the reference sphere. For example, when the operator wishes to increase the resolution, the diameter of the reference sphere can be increased, and the curvature of the spherical surface on which the detection surface of each detection element is located can be increased accordingly. When the operator wishes to increase the X-ray intensity, the diameter of the reference sphere can be decreased, and the curvature of the spherical surface on which the detection surface of each detection element is located can be decreased accordingly. In both analytical modes, the curvature of the spherical surface on which the detection surface of each detection element is located can be changed with great precision, and a more accurate analysis can be performed.

Effect of the Invention

In the present invention, an analysis can be performed in less time by detecting X-rays diffracted by the specimen using a plurality of detection elements, and errors in the X-ray intensity detected by each detection element can be eliminated to perform a more accurate analysis.

DETAILED DESCRIPTION OF THE EXEMPLARY EMBODIMENTS

Figure 1:
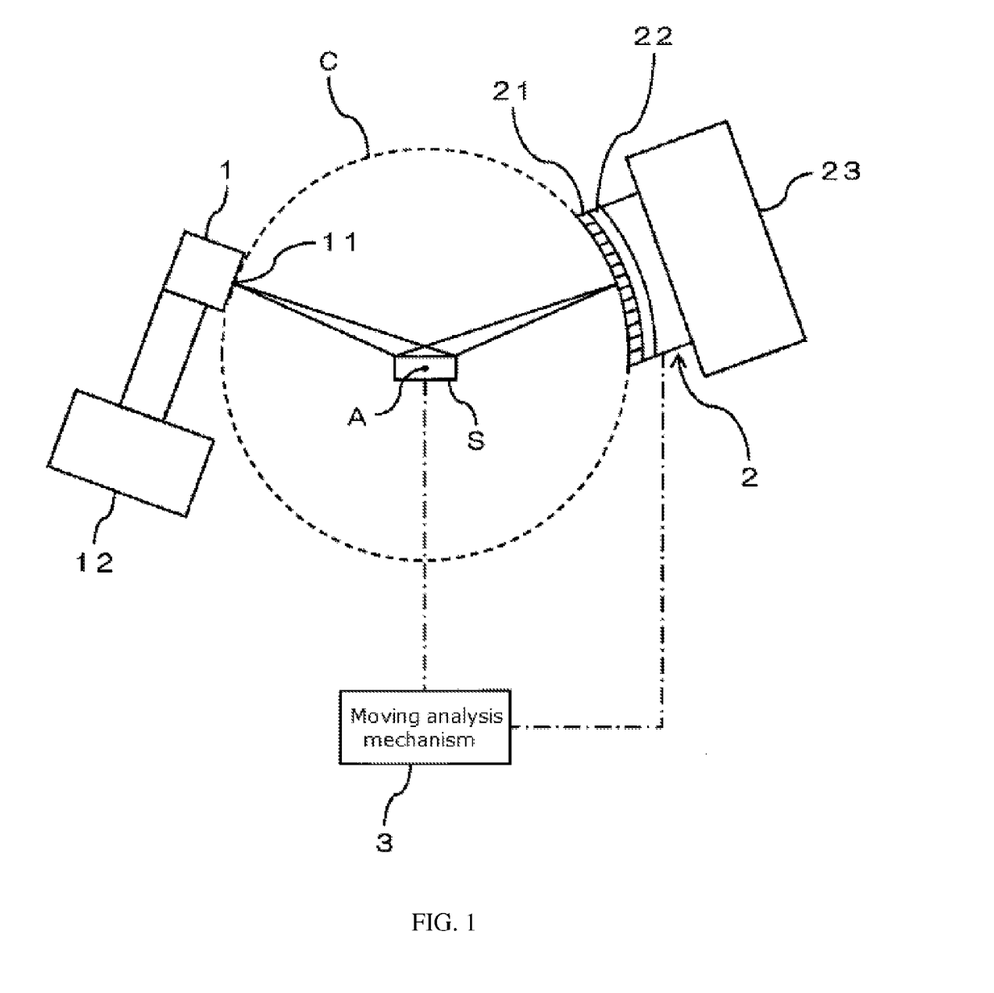
FIG. 1 is a schematic view showing the configuration of the X-ray analyzer in an embodiment of the present invention.

FIG. 1 is a schematic view showing the configuration of the X-ray analyzer in an embodiment of the present invention. This X-ray analyzer includes an X-ray source 1 for exposing a specimen S to X-rays, and a detector 2 for detecting X-rays diffracted by the specimen S.

The X-ray source 1 and the detector 2 are located on a diffractometer circle (reference circle) C centered on the specimen S. The X-ray source 1 radiates X-rays from an X-ray focal point 11 positioned on the diffractometer circle C. The detector 2 has a plurality of detection elements 21 on a substrate 22, and X-rays diffracted by the specimen S can be detected by each of the detection elements 21.

In this example, the specimen S and the detector 2 can be rotated using the center A of the diffractometer circle C as the axis of rotation. A moving analysis mechanism 3 rotates the specimen S and the detector 2 so that the X-ray source 1 and the detector 2 can move relative to each other on the diffractometer circle C during the analysis. The moving analysis mechanism 3 includes a drive source such as a motor (not shown) and can simultaneously rotate the specimen S and the detector 2.

More specifically, using the center A of the diffractometer circle C as the axis of rotation, the specimen S can be rotated at a predetermined angular velocity (so-called θ rotation) to change the angle of incidence of the X-rays from the X-ray source 1 relative to the surface of the specimen S. At this time, the detector 2 is rotated on the axis of rotation at an angular velocity twice that of the θ rotation (so-called 2θ rotation). In this way, diffraction information is obtained while holding constant the relationship between the angle of incidence of the X-rays from the X-ray source 1 relative to the specimen S and the angle of incidence to the detector 2 of the X-rays diffracted by the specimen S.

The moving analysis mechanism 3 is not limited to a configuration in which the specimen S and the detector 2 are rotated relative to a stationary X-ray source 1. For example, the X-ray source 1 and the detector 2 may be rotated using the center A of the diffractometer circle C as the axis of rotation while the specimen S remains stationary, or the specimen S and the X-ray source 1 may be rotated using the center A of the diffractometer circle C as the axis of rotation while the detector 2 remains stationary. In either case, diffraction information is obtained while holding constant the relationship between the angle of incidence of the X-rays from the X-ray source 1 relative to the specimen S and the angle of incidence to the detector 2 of the X-rays diffracted by the specimen S.

The X-ray source 1 can use an X-ray distance changing mechanism 12 to move the X-ray source 1 in the radial direction relative to the center A of the diffractometer circle C. In this way, the distance of the X-ray source 1 (X-ray focal point 11) can be changed relative to the specimen S. The detector 2 can also use a detection distance changing mechanism 23 to move the detector 2 in the radial direction relative to the center A of the diffractometer circle C. In this way, the distance of the detector 2 can be changed relative to the specimen S.

The X-ray distance changing mechanism 12 and the detection distance changing mechanism 23 have a drive source such as a motor (not shown), and the simultaneous moving of the X-ray source 1 and the detector 2 can be used to keep the X-ray source 1 and the detector 2 at the same distance from the specimen S. In this way, the diameter of the diffractometer circle C can be changed. In other words, the X-ray distance changing mechanism 12 and the detection distance changing mechanism 23 moving the X-ray source 1 and the detector 2 function as a reference circle changing mechanism used to change the diameter of the diffractometer circle C.

The reference circle changing mechanism is not limited to a configuration in which the X-ray source 1 and the detector 2 are moved relative to a stationary specimen S. For example, the specimen S and the detector 2 can be moved relative to a stationary X-ray source 1, or the specimen S and the X-ray device 1 can be moved relative to a stationary detector 2. In both cases, the diameter of the diffractometer circle C can be changed while keeping the distance of the X-ray source 1 and the detector 2 the same relative to the specimen S.

In the present embodiment, as shown in FIG. 1, each of the detection elements 21 in the detector 2 is located along the diffractometer circle C. The following is a detailed description of specific examples with reference to FIG. 2A and FIG. 2B.

Figure 2A:
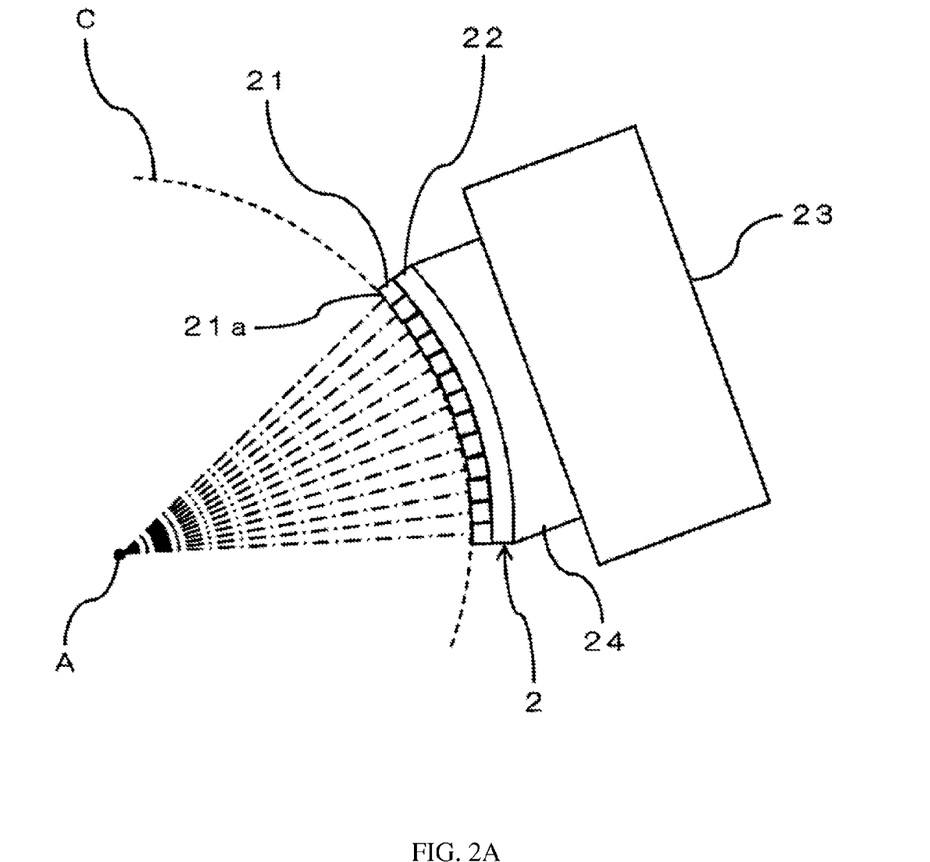
FIG. 2A is a schematic diagram showing the configuration of the detector in FIG. 1.

FIG. 2A is a schematic diagram showing the configuration of the detector 2 in FIG. 1. In this example, the substrate 22 of the detector 2 is a flexible substrate. The flexible substrate is a substrate made of a flexible material that can be deformed and bent by the application of external force.

A plurality of detection elements 21 are arranged in a single row on the substrate 22. Any number of detection elements 21 can be arranged on the substrate 22. Each of the detection elements 21 has a detection surface 21a incident on X-rays diffracted by a specimen S. Each detection surface 21a is on the same plane when the substrate 22 is flat. The width of the detection surface 21a of each detection element 21 can be, for example, 50 μm.

Because the substrate 22 in this example is a flexible substrate, the relative position of the detection surface 21a of each detection element 21 can be changed by bending the substrate 22. More specifically, the detection surface 21a of each detection element 21 can be positioned on an arc along the diffractometer circle C by bending the substrate 22. In this case, the detection surface 21a of each detection element 21 faces the center A of the diffractometer circle C as shown in FIG. 2A. In other words, each detection surface 21a is positioned so as to extend along a tangent line of the diffractometer circle C.

During an analysis, the detector 2 is moved so as to intermittently or continuously move the detection elements 21 on the diffractometer circle C and obtain diffraction information on the basis of the X-ray intensity incident on the detection surface 21a of each detection element 21. Because X-rays diffracted by the specimen S can be detected by the detection elements 221 at the same time, the time required to perform an analysis can be reduced. When diffraction information is obtained on the basis of the X-ray intensity detected by each detection element 21, the position information for each detection element 21 is converted to angle information on the diffractometer circle C centered on the axis of rotation.

Because, in the present embodiment, the detection surface 21a of each detection element 21 is located on an arc along the diffractometer circle C, each detection element 21 can detect X-rays diffracted by the specimen S at the focal point. Because this prevents errors in the X-ray intensity detected by each detection element 21, more accurate diffraction information can be obtained. As a result, a more accurate analysis can be performed in less time by detecting X-rays diffracted by the specimen S using a plurality of detection elements 21.

Also, because the detection surface 21a of each detection element 21 is located on an arc along the diffractometer circle C, angle correction is not required when the position information of each detection element 21 is converted to angle information. As a result, accurate analysis can be performed without requiring angle correction.

Because the detection surface 21a of each detection element 21 faces the center A of the diffractometer circle C, the X-rays diffracted by the specimen S are incident at a right angle on the detection surface 21a of each detection element 21. In this way, errors in the X-ray intensity detected by each detection element 21 are more effectively prevented, and an even more accurate analysis is performed.

In the present embodiment, the detection surface 21a of each detection element 21 can be positioned on an arc along the diffractometer circle C and the detection surfaces 21a oriented towards the center A of the diffractometer circle C simply by bending the flexible substrate 22. As a result, a very simple configuration for obtaining an accurate analysis can be realized.

In the present embodiment, as shown in FIG. 2A, a substrate-deforming mechanism 24 is mounted on the detector 22 to move the detection elements 21 relative to each other by changing the amount by which the substrate 22 of the detector 2 is bent. This substrate-deforming mechanism 24 functions as an arc curvature changing mechanism for changing the curvature of the arc on which the detection surface 21a of each detection element 21 is located.

In the substrate-deforming mechanism 24, the center can be displaced while keeping the ends of the substrate 22 stationary, or the ends can be displaced while keeping the center of the substrate 22 stationary. In either case, the center or ends of the substrate 22 can be displaced using a mechanical or electrical displacing mechanism.

The mechanical or electrical displacing mechanism can use a piezoelectric element, or an actuator such as a solenoid. Instead of using a piezoelectric element or actuator, the amount by which the substrate 22 is bent can be changed by using suction to hold the central portion of the substrate 22 and using the change in pressure to displace the central portion of the substrate 22.

When the X-ray distance changing mechanism 12 and the detection distance changing mechanism 23 constituting the reference circle changing mechanism move the X-ray source 1 and the detector 2 to change the diameter of the diffractometer circle C, the substrate-deforming mechanism 24 can be operated accordingly. More specifically, the curvature of the arc on which the detection surface 21a of each detection element 21 is located can be changed to correspond to the changed curvature of the diffractometer C, and the detection surfaces 21a can be kept on the arc along the diffractometer circle C.

In the present embodiment, because the curvature of the arc on which the detection surface 21a of each detection element 21 is located is changed, the incident aspect of each detection surface 21a can be changed relative to the X-rays diffracted by the specimen S, and an analysis can be performed using a wider aspect.

More specifically, in the present embodiment, the curvature of the arc on which the detection surface 21a of each detection element 21 is located can be changed to correspond to any change in the radius of the diffractometer circle C. For example, when the operator wishes to increase the resolution, the diameter of the diffractometer circle C can be increased, and the curvature of the arc on which the detection surface 21a of each detection element 21 is located can be increased accordingly. When the operator wishes to increase the X-ray intensity, the diameter of the diffractometer circle C can be decreased, and the curvature of the arc on which the detection surface 21a of each detection element 21 is located can be decreased accordingly. In both analytical modes, the curvature of the arc on which the detection surface 21a of each detection element 21 is located can be changed with great precision, and a more accurate analysis can be performed.

Figure 2B:
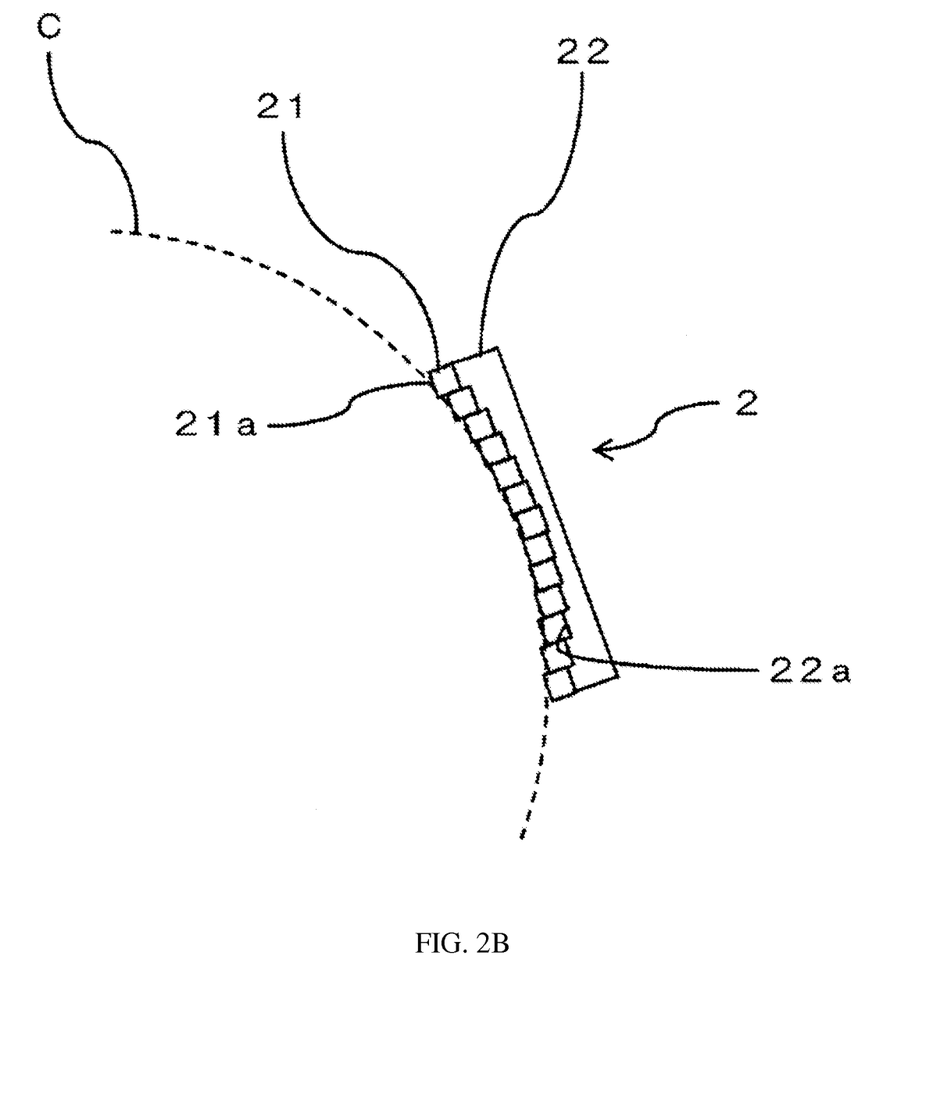
FIG. 2B is a schematic diagram showing another configuration of the detector in FIG. 1.

FIG. 2B is a schematic diagram showing another configuration of the detector 2 in FIG. 1. In this example, the substrate 22 of the detector 2 is a rigid substrate such as a glass epoxy substrate.

A plurality of detection elements 21 are arranged in a single row on the substrate 22. Any number of detection elements 21 can be arranged on the substrate 22. A plurality of tiered surfaces 22a are formed on the surface of the substrate 22 in positions corresponding to the mounting positions for each detection element 21. Each tiered surface 22a is formed with flat parallel surfaces, which are gradually lowered towards the center from both ends of the substrate 22.

In this way, the detection surface 21a of each detection element 21 mounted on each tiered surface 22a of the substrate 22 are parallel but at different heights in stages. In this example, the detection surface 21a of each detection element 21 is located on an arc along the diffractometer circle C. Here, the concept of each detection surface 21a being positioned on an arc corresponding to the diffractometer circle C does not only mean, as shown in FIG. 2A, that each detection surface 21a is located smoothly on an arc along the diffractometer circle C, but also, as shown in FIG. 2B, that each detection surface 21a is positioned in stages along the diffractometer circle C.

Because, as shown in FIG. 2B, the detection surface 21a of each detection element 21 is located on an arc along the diffractometer circle C, each detection element 21 can detect X-rays diffracted by the specimen S at the focal point. Because this prevents errors in the X-ray intensity detected by each detection element 21, more accurate diffraction information can be obtained. As a result, a more accurate analysis can be performed in less time by detecting X-rays diffracted by the specimen S using a plurality of detection elements 21.

Also, because the detection surface 21a of each detection element 21 is located on an arc along the diffractometer circle C, angle correction is not required when the position information of each detection element 21 is converted to angle information. As a result, accurate analysis can be performed without requiring angle correction.

Figure 3:
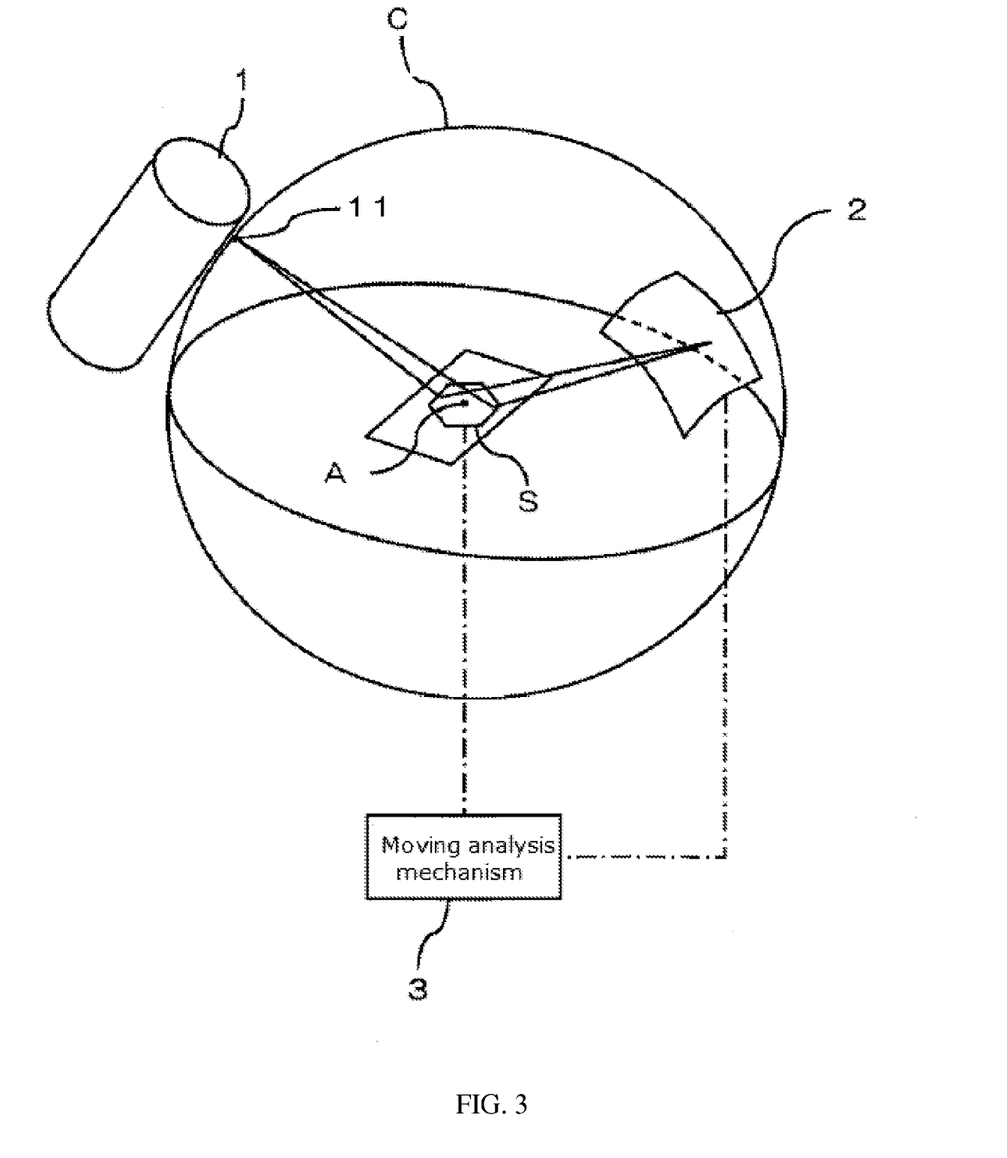
FIG. 3 is a schematic view showing the configuration of the X-ray analyzer in another embodiment of the present invention.

FIG. 3 is a schematic view showing the configuration of the X-ray analyzer in another embodiment of the present invention. As in the previous embodiment, this X-ray detector includes an X-ray source 1 for exposing a specimen S to X-rays, and a detector 2 for detecting X-rays diffracted by the specimen S.

In the present embodiment, the X-ray source 1 and the detector 2 are located on a diffractometer sphere (reference sphere) C' centered on the specimen S. The X-ray source 1 radiates X-rays from an X-ray focal point 11 positioned on the diffractometer sphere C'. In this example, the specimen S and the detector 2 can be rotated three-dimensionally using the center A' of the diffractometer sphere C' as the axis of rotation.

The specimen S and the detector 2 are rotated by the moving analysis mechanism 3, and an analysis is performed as the X-ray source 1 and the detector 2 move relative to each other on the diffractometer sphere C'. The moving analysis mechanism 3 includes a drive source such as a motor (not shown) and can simultaneously rotate the specimen S and the detector 2. Because the relative movement of the X-ray source 1 and the detector 2 by the moving analysis mechanism 3 is the same as that in the previous embodiment, detailed explanation of this relative movement is omitted here.

Figure 4:
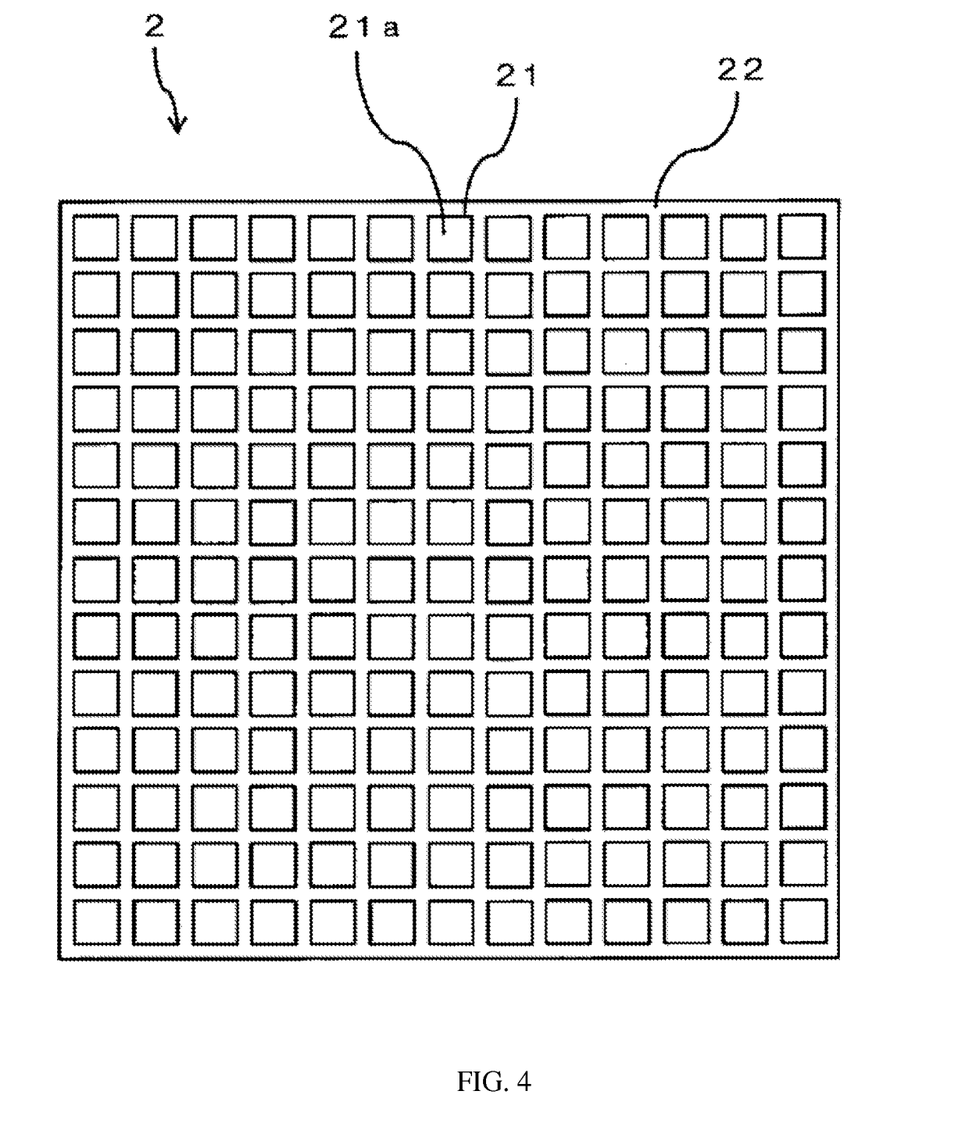
FIG. 4 is a schematic diagram showing the configuration of the detector in FIG. 3.

FIG. 4 is a schematic diagram showing the configuration of the detector 2 in FIG. 3. The detector 2 has a plurality of detection elements 21 on a substrate 22, and X-rays diffracted by the specimen S can be detected by each detection element 21. In this example, the substrate 22 of the detector 2 is a flexible substrate.

A plurality of detection elements 21 are arranged in a grid on the substrate 22. Any number of detection elements 21 can be arranged on the substrate 22. Each of the detection elements 21 has a detection surface 21a incident on X-rays diffracted by a specimen S. Each detection surface 21a is on the same plane when the substrate 22 is flat. The width of the detection surface 21a of each detection element 21 can be, for example, 50 μm.

Because the substrate 22 in this example is a flexible substrate, the relative position of the detection surface 21a of each detection element 21 can be changed by bending the substrate 22. More specifically, the detection surface 21a of each detection element 21 can be positioned on a spherical surface along the diffractometer sphere C' by bending the substrate 22. In this case, the detection surface 21a of each detection element 21 faces the center A' of the diffractometer sphere C'.

Because, in the present embodiment, the detection surface 21a of each detection element 21 is located on a spherical surface along the diffractometer sphere C', each detection element 21 can detect X-rays diffracted by the specimen S at the focal point. Because this prevents errors in the X-ray intensity detected by each detection element 21, more accurate diffraction information can be obtained. As a result, a more accurate analysis can be performed in less time by detecting X-rays diffracted by the specimen S using a plurality of detection elements 21.

Also, because the detection surface 21a of each detection element 21 is located on a spherical surface along the diffractometer sphere C', angle correction is not required when the position information of each detection element 21 is converted to angle information. As a result, accurate analysis can be performed without requiring angle correction.

Because the detection surface 21a of each detection element 21 faces the center A' of the diffractometer sphere C', the X-rays diffracted by the specimen S are incident at a right angle on the detection surface 21a of each detection element 21. In this way, errors in the X-ray intensity detected by each detection element 21 are more effectively prevented, and an even more accurate analysis is performed.

In the present embodiment, the detection surface 21a of each detection element 21 can be positioned on a spherical surface along the diffractometer sphere C' and the detection surfaces 21a oriented towards the center A' of the diffractometer sphere C' simply by bending the flexible substrate 22. As a result, a very simple configuration for obtaining an accurate analysis can be realized.

While not shown in FIG. 3, the present embodiment includes an X-ray distance changing mechanism 12 and a detection distance changing mechanism 23 similar to the ones in FIG. 1. Here, the X-ray source 1 uses the X-ray distance changing mechanism 12 that can move the X-ray source 1 in the radial direction relative to the center A' of the diffractometer sphere C'. In this way, the distance of the X-ray source 1 (X-ray focal point 11) can be changed relative to the specimen S. The detector 2 can use the detection distance changing mechanism 23 to move the detector 2 in the radial direction relative to the center A' of the diffractometer sphere C'. In this way, the distance of the detector 2 can be changed relative to the specimen S.

In other words, the X-ray distance changing mechanism 12 and the detection distance changing mechanism 23 moving the X-ray source 1 and the detector 2 function as a reference sphere changing mechanism used to change the diameter of the diffractometer sphere C'.

While not shown in FIG. 3, the present embodiment includes a substrate-deforming mechanism 24 for changing the amount of curvature in the substrate 22 of the detector 2 as shown in FIG. 2A. Here, the substrate-deforming mechanism 24 functions as a spherical curvature changing mechanism for changing the curvature of the sphere on which the detection surface 21a of each detection element 21 is located by moving the detection elements 21 relative to each other.

When the X-ray distance changing mechanism 12 and the detection distance changing mechanism 23 constituting the reference sphere changing mechanism move the X-ray source 1 and the detector 2 relative to each other and change the radius of the diffractometer sphere C', the substrate-deforming mechanism 24 operates accordingly. More specifically, the curvature of the spherical surface on which the detection surface 21a of each detection element 21 is located is changed so as to correspond to the curvature of the changed diffractometer sphere C', and the location of each detection surface 21a is maintained on the spherical surface along the diffractometer sphere C'.

In the present embodiment, because the curvature of the spherical surface on which the detection surface 21a of each detection element 21 is located is changed, the incident aspect of the detection surface 21a of each detection element 21 can be changed relative to the X-rays diffracted by the specimen S, and an analysis can be performed using a wider aspect.

More specifically, in the present embodiment, the curvature of the spherical surface on which the detection surface 21a of each detection element 21 is located can be changed to correspond to any change in the radius of the diffractometer sphere C'. For example, when the operator wishes to increase the resolution, the diameter of the diffractometer sphere C' can be increased, and the curvature of the spherical surface on which the detection surface 21a of each detection element 21 is located can be increased accordingly. When the operator wishes to increase the X-ray intensity, the diameter of the diffractometer sphere C' can be decreased, and the curvature of the spherical surface on which the detection surface 21a of each detection element 21 is located can be decreased accordingly. In both analytical modes, the curvature of the spherical surface on which the detection surface 21a of each detection element 21 is located can be changed with great precision, and a more accurate analysis can be performed.

The substrate 22 of the detector 2 does not have to be a flexible substrate. It may also be a rigid substrate as shown in FIG. 2B. Here, a plurality of tiered surfaces are formed, for example, so that the tiered surfaces are gradually lowered from the corners to the center of a rectangular substrate 22, and a detection element 21 is mounted on each tiered surface so that the detection surface 21a of each detection element 21 is located on a spherical surface along the diffractometer sphere C'.

KEY TO THE FIGURES

1: X-ray source
2: Detector
3: Moving analysis mechanism
11: X-ray focal point
12: X-ray distance changing mechanism
21: Detection element
21a: Detection surface
22: Substrate
22a: Tiered surface
23: Detection distance changing mechanism
24: Substrate-deforming mechanism
S: Specimen
A: Center
A': Center
C: Diffractometer circle
C': Diffractometer sphere

What is claimed:
1. An X-ray analyzer comprising:
an X-ray source for exposing a specimen to X-rays;
a detector having a plurality of detection elements, each detection element detecting X-rays diffracted by the specimen;
a moving analysis mechanism for moving the X-ray source and detector relative to a reference circle centered on the specimen while performing an analysis; and
a flexible substrate on which the plurality of detection elements are arranged,
wherein a detection surface of each detection element is located on an arc along the reference circle, and
the flexible substrate is configured to be deformed so as to change the curvature of the arc on which the detection surface of each detection element is located.

2. The X-ray analyzer according to claim 1, wherein the detection surface of each detection element faces the center of the reference circle.

3. The X-ray analyzer according to claim 2, the plurality of detection elements are arranged in a single row on the flexible substrate.

4. The X-ray analyzer according to claim 1 wherein the X-ray source and the detector are configured to move relative to each other to change the radius of the reference circle, and
the curvature of the arc on which the detection surface of each detection element is located is configured to change so as to correspond to the curvature of the reference circle changed by the reference circle changing mechanism.

5. An X-ray analyzer comprising:
an X-ray source for exposing a specimen to X-rays;
a detector having a plurality of detection elements, each detection element detecting X-rays diffracted by the specimen;
a moving analysis mechanism for moving the X-ray source and detector relative to a reference sphere centered on the specimen while performing an analysis;
a flexible substrate on which the plurality of detection elements are arranged,
wherein a detection surface of each detection element is located on a spherical surface along the reference sphere, and
the flexible substrate is configured to be deformed so as to change the curvature of the sphere on which the detection surface of each detection element is located.

6. The X-ray analyzer according to claim 5, wherein the detection surface of each detection element faces the center of the reference sphere.

7. The X-ray analyzer according to claim 6, wherein the detector is composed by arranging the plurality of detection elements in a grid pattern on a flexible substrate,
the detection surface of each detection element being located on a spherical surface along the reference sphere by curving the flexible substrate.

8. The X-ray analyzer according to claim 5 wherein the X-ray source and the detector are configured to move relative to each other to change the radius of the reference, sphere, and
the curvature of the sphere on which the detection surface of each detection element is located is configured to change so as to correspond to the curvature of the reference sphere changed by the reference sphere changing mechanism.

* * * * *